United States Patent [19]

Foxton et al.

[11] 4,208,517

[45] Jun. 17, 1980

[54] CEPHALOSPORIN COMPOUNDS HAVING AT POSITION-7 AN α-ETHERIFIED HYDROXYIMINOARYLACETAMIDO GROUP

[75] Inventors: Michael W. Foxton, Chalfont St. Giles; Gordon I. Gregory, Chalfont St. Peter; David M. Rogers, Ulverston, all of England

[73] Assignee: Glaxo Operations UK Limited, Greenford, England

[21] Appl. No.: 855,080

[22] Filed: Nov. 28, 1977

[30] Foreign Application Priority Data

Nov. 30, 1976 [GB] United Kingdom ............... 49961/76

[51] Int. Cl.² ................. A61K 31/545; C07D 501/32; C07D 501/34
[52] U.S. Cl. ...................................... 544/28; 544/22; 544/30; 544/27; 260/553 R; 424/246
[58] Field of Search ............................ 544/28, 22, 30; 424/246

[56] References Cited

U.S. PATENT DOCUMENTS

| 3,687,949 | 8/1972 | Holdrege ................................. 544/30 |
| 4,074,047 | 2/1978 | Foxton et al. ........................ 544/27 |

FOREIGN PATENT DOCUMENTS 2460537 7/1975 Fed. Rep. of Germany .

*Primary Examiner*—Donald G. Daus
*Assistant Examiner*—David E. Wheeler
*Attorney, Agent, or Firm*—Bacon & Thomas

[57] ABSTRACT

Antibiotic compounds of the general formula

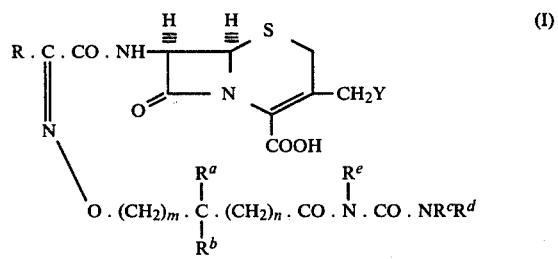

[wherein R is a phenyl, thienyl or furyl group; $R^a$ and $R^b$, which may be the same or different, are each selected from hydrogen, $C_{1-4}$ alkyl, $C_{2-4}$ alkenyl, $C_{3-7}$ cycloalkyl, phenyl, naphthyl, thienyl, furyl, carboxy, $C_{2-5}$ alkoxycarbonyl and cyano, or $R^a$ and $R^b$ together wth the carbon atom to which they are attached form a $C_{3-7}$ cycloalkylidene or cycloalkenylidene group; $R^c$ and $R^d$, which may be the same or different, each represents a hydrogen atom or a substituting group e.g. an alkyl group or substituted alkyl group; or $R^c$ and $R^d$ together with the nitrogen atom to which they are attached form a saturated or unsaturated heterocyclic ring which contains 5–7 ring members and which may contain additional hetero atoms, and may be substituted by lower alkyl; $R^e$ represents hydrogen or $C_{1-4}$ alkyl; m and n are each 0 or 1 such that the sum of m and n is 0 or 1 and Y is selected from various oxygen and sulphur nucleophiles] and non-toxic derivatives thereof.

11 Claims, No Drawings

CAPHALOSPORIN COMPOUNDS HAVING AT POSITION-7 AN α-ETHERIFIED HYDROXYIMINOARYLACETAMIDO GROUP

This invention is concerned with improvements in or relating to cephalosporin compounds, and is more particularly concerned with a novel class of cephalosporin compounds possessing valuable antibiotic properties.

The cephalosporin compounds in this specification are named with reference to "cepham" after *J. Amer. Chem. Soc.*, 1962, 84, 3400, the term "cephem" referring to the basic cepham structure with one double bond.

Cephalosporin antibiotics are widely used in the treatment of diseases caused by pathogenic bacteria in human beings and animals, and are especially useful in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both gram positive and gram negative microorganisms, and a significant amount of research has been directed to the development of various types of broad spectrum cephalosporin antibiotics.

Considerable interest is currently being directed to the development of broad spectrum cephalosporin antibiotics which possess high activity against gram negative organisms. Existing commercially available β-lactam antibiotics tend to exhibit comparatively low activity against certain gram negative organisms, e.g. β-lactamase producing organisms, which are an increasingly common source of infection in humans. The practical therapeutic applications of aminoglycoside antibiotics such as gentamicin which do exhibit activity against gram negative organisms tend to be limited or complicated by the high toxicity of these antibiotics. It is well known that cephalosporin antibiotics normally exhibit low toxicity in man, so that the development of broad spectrum cephalosporin antibiotics possessing high activity against gram negative organisms such as strains of *Escherichia coli* fulfils a significant need in chemotheraphy.

The present invention is concerned with 7β-acylamidoceph-3-em-4-carboxylic acid antibiotics and non-toxic derivatives thereof which are characterised in that the said acylamido moiety has the formula

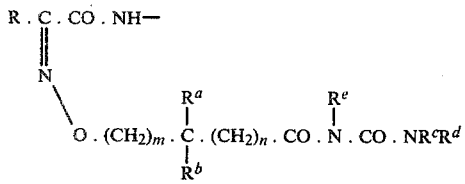

[wherein R is a phenyl, thienyl or furyl group; $R^a$ and $R^b$, which may be the same or different, are each selected from hydrogen, $C_{1-4}$ alkyl (e.g. methyl, ethyl, n-propyl, isopropyl or butyl), $C_{2-4}$ alkenyl (e.g. vinyl or allyl), $C_{3-7}$ cycloalkyl (e.g. cyclopropyl, cyclobutyl, cyclopentyl or cyclohexyl), phenyl, naphthyl, thienyl, furyl, carboxy, $C_{2-5}$ alkoxycarbonyl (e.g. ethoxycarbonyl) and cyano, or $R^a$ and $R^b$ together with the carbon atom to which they are attached form a $C_{3-7}$ cycloalkylidene or cycloalkenylidene group (e.g. a cyclobutylidene, cyclopentylidene or cyclohexylidene group); $R^c$ and $R^d$, which may be the same or different, each represents a hydrogen atom or a substituting group e.g. an alkyl group or substituted alkyl group (e.g. a methyl, ethyl, propyl, isopropyl or t-butyl group); or $R^c$ and $R^d$ together with the nitrogen atom to which they are attached form a saturated or unsaturated heterocyclic ring which contains 5–7 ring members and which may contain additional hetero atoms, e.g. N, O or S and may be substituted by lower alkyl; $R^e$ represents hydrogen or $C_{1-4}$ alkyl (e.g. methyl, ethyl, n-propyl, isopropyl or butyl); and m and n are each 0 or 1 such that the sum of m and n is 0 or 1].

The antibiotic compounds of the present invention may be represented as compounds of the general formula

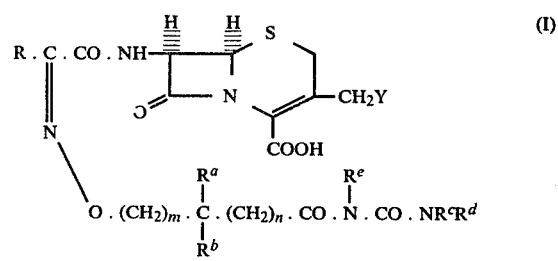

[where R, $R^a$, $R^b$, $R^c$, $R^d$, $R^e$, m and n are as hereinbefore defined and Y is the residue of an oxygen or sulphur nucleophile] and non-toxic derivatives thereof.

These compounds are syn isomers or existing as mixtures of syn and anti isomers containing at least 75% of the syn isomer, preferably at least 90% of the syn isomer.

The antibiotic compounds of formula I may be used to treat a wide variety of diseases caused by pathogenic bacteria in human beings and animals such as respiratory tract and urinary tract infections.

These compounds exhibit broad spectrum antibiotic activity. The compounds exhibit activity against microorganisms which produce β-lactamases, and also possess very high stability to β-lactamases produced by a range of gram negative organisms.

Compounds according to the invention have been found to exhibit good activity against various members of the Enterobacteriaceae (e.g. strains of *Escherichia coli*, *Klebsiella aerogenes* and *Proteus mirabilis*).

Compounds wherein at least one of $R^a$ and $R^b$ is other than hydrogen have also shown activity against Pseudomonas organisms e.g. strains of *Pseudomonas aeruginosa*.

The compounds of the invention are defined as having the syn isomeric form as regards the configuration of the group

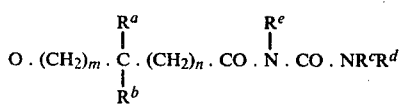

with respect to the carboxamido group. In this specification the syn configuration is denoted structurally as

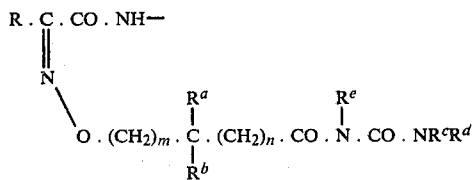

this configuration being assigned on the basis of the work of Ahmad and Spenser reported in *Can. J. Chem.,* 1961, 39, 1340. As indicated above, the compounds may exist as mixtures of syn and anti isomers provided that such mixtures contain at least 75% of the syn isomer, preferably at least 90% of the syn isomer. We prefer, however, the compounds to be syn isomers essentially free from the corresponding anti isomer.

By "non-toxic derivatives" is meant those derivatives which are physiologically acceptable in the dosage at which they are administered. Such derivatives may include, for example, salts, biologically acceptable esters, 1-oxides and solvates (especially hydrates). It will be appreciated that where $R^a$ or $R^b$ is carboxy, derivatives such as salts and esters may be formed by reaction of either or both of the carboxy groups present in such compounds of formula I.

Non-toxic salt derivatives which may be formed from the compounds of general formula I include inorganic base salts such as alkali metal salts (e.g. sodium and potassium salts) and alkaline earth metal salts (e.g. calcium salts); organic base salts (e.g. procaine, phenylethylbenzylamine, dibenzylethylenediamine, ethanolamine, diethanolamine, triethanolamine and N-methylglucosamine salts); and, where appropriate, acid addition salts, e.g. with hydrochloric, hydrobromic, sulphuric, nitric, phosphoric, trifluoroacetic, toluene-p-sulphonic and methane sulphonic acids. The salts may also be in the form of resinates formed with, for example, a polystyrene resin or cross-linked polystyrene divinylbenzene copolymer resin containing amino or quaternary amino groups, or, where appropriate, sulphonic acid groups, or, again where appropriate, with a resin containing carboxyl groups, e.g. a polyacrylic acid resin. Use of highly soluble base salts (e.g. alkali metal salts such as the sodium salt) of compounds of formula I is generally advantageous in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

Biologically acceptable, metabolically labile ester derivatives which may be formed from compounds of formula I include, for example, acyloxymethyl esters, e.g. lower alkanoyloxymethyl esters such as acetoxymethyl, acetoxyethyl or pivaloyloxymethyl esters.

It will be appreciated that when $R^a$ and $R^b$ in the above formulae are different, the carbon atom to which they are attached may comprise a centre of asymmetry; compounds in accordance with the invention wherein $R^a$ and $R^b$ are different may thus be diastereoisomeric. The invention embraces the individual diastereoisomers of such compounds as well as mixtures thereof.

The groups Y in formula (I) above may be derived from a wide variety of sulphur nucleophiles.

Examples of sulphur nucleophiles include thioureas, including aliphatic, aromatic, araliphatic, alicyclic and heterocyclic substituted thioureas; dithiocarbamates; aromatic, aliphatic and cyclic thioamides, for example thioacetamide and thiosemicarbazide; thiosulphates; thiols; thiophenols; thioacids, e.g. thiobenzoic acid or thiopicolinic acid; and dithioacids.

One class of sulphur nucleophile includes those compounds of the formula: $R^1.S(O)_nH$ in which $R^1$ is an aliphatic e.g. lower alkyl such as methyl, ethyl or n-propyl group; an alicyclic e.g. lower cycloalkyl such as cyclohexyl or cyclopentyl group; an aromatic e.g. $C_{6-12}$ mono- or bicyclic carbocyclic aryl such as phenyl or naphthyl group; an araliphatic e.g. phenyl lower (e.g. $C_{1-4}$) alkyl such as benzyl group; or a heterocyclic group, and n is 0, 1 or 2. A preferred class of nucleophiles falling within the above formula is that having the general formula $R^2SH$ in which $R^2$ is aliphatic e.g. lower alkyl such as methyl, ethyl or n-propyl or lower alkanoyl such as acetyl; araliphatic, e.g. lower alkyl such as methyl, ethyl or n-propyl or lower alkanoyl such as acetyl; araliphatic, e.g. phenyl lower alkyl such as benzyl or phenethyl or substituted phenyl lower alkyl; alicyclic, e.g. cycloalkyl such as cyclopentyl or cyclohexyl; aromatic, e.g. phenyl, substituted phenyl or a heterocyclic group containing at least one 5- or 6-membered ring and having one or more heteroatoms selected from O, N and S. Such heterocyclic groups $R^2$ may be substituted, and examples of suitable heterocyclic groups include thiadiazolyl, e.g. 5-methyl-1,3,4-thiadiazol-2-yl; diazolyl; triazolyl, e.g. triazol-4-yl; tetrazolyl, e.g. 1-methyltetrazol-5-yl, 1-ethyltetrazol-5-yl, 1-phenyltetrazol-5-yl or 1-carboxymethyltetrazol-5-yl; thiazolyl; thiatriazolyl; oxazolyl; oxadiazolyl, e.g. 2-phenyl-1,3,4-oxadiazol-5-yl; pyridyl, e.g. N-methylpyrid-2-yl; pyrimidyl; fused heterocyclic ring systems such as benzimidazolyl, benzoxazolyl, benzothiazolyl such as benzothiazol-2-yl, triazolpyridyl or purinyl; and substituted versions of such fused ring systems, e.g. nitrobenzothiazol-2-yl such as 5- or 6-nitrobenzothiazol-2-yl.

The group Y in formula (I) above may also be derived from a wide variety of oxygen nucleophiles. Examples of oxygen nucleophiles include water; alcohols, for example alkanols such as methanol, ethanol, propanol and butanol; and lower alkanoic and alkenoic acids.

The term "oxygen nucleophile" thus includes compounds of the following formula:

$$R^3OH$$

in which the group $R^3$ may be lower alkyl (e.g. methyl, ethyl, n-propyl, isopropyl, n-butyl or isobutyl); lower alkenyl (e.g. allyl); lower alkynyl (e.g. propynyl); lower cycloalkyl (e.g. cyclopropyl, cyclopentyl or cyclohexyl); lower cycloalkyl lower alkyl (e.g. cyclopropylmethyl, cyclopentylmethyl or cyclohexylethyl); aryl (e.g. phenyl or naphthyl) aryl lower alkyl (e.g. benzyl); heterocyclic (e.g. a heterocyclic group as defined for $R^2$, such as N-methylpyrid-2-yl); heterocyclic lower alkyl (e.g. furfuryl); or any of these groups substituted by, for example, one or more of lower alkoxy (e.g. methoxy or ethoxy), lower alkylthio (e.g. methylthio or ethylthio), halogen (chlorine, bromine, iodine or fluorine), lower alkyl (e.g. methyl or ethyl), nitro, hydroxy, acyloxy, carboxy, carbalkoxy, lower alkylcarbonyl, lower alkylsulphonyl, lower alkoxysulphonyl, amino, lower alkylamino or acylamino groups.

In the case in which water is the nucleophile there will be obtained 3-hydroxymethyl cephalosporin compounds. Such 3-hydroxymethyl compounds and non-toxic derivatives thereof may show antibacterial activity and it is of note that they may be metabolites of compounds of general formula I where Y is acetoxy 3-Hydroxymethyl cephalosporins may be acylated to form derivatives characterized by possessing the group 3—$CH_2.O.CO.R^4$ or 3—$CH_2.O.CO.AR^5$ where A is O, S or NH, $R^4$ is an organic group and $R^5$ is hydrogen or an organic group.

The group $R^4CO$— or $R^5A.CO$— may be chosen from among the wide class of such groups described in the literature and may have up to 20 carbon atoms. $R^4$ and, where appropriate, $R^5$ may thus each be a hydrocarbon group or such a group carrying one or more substituent atoms or groups, and may thus be chosen from the following list, which is not intended to be exhaustive:

(i) $C_nH_{2n+1}$ where n is an integer from 1 to 7, e.g. 1 to 4. The group may be straight or branched and, if desired, may be interrupted by an oxygen or sulphur atom or an imino group or substituted by cyano, carboxy, lower alkoxycarbonyl, hydroxy, carboxycarbonyl (HOOC.CO.), halogen (e.g. chlorine, bromine or iodine) or amino. Examples of such groups include methyl, ethyl, propyl, isopropyl, n-butyl, t-butyl, sec.butyl and 2-chloroethyl.

(ii) $C_nH_{2n-1}$ where n is an integer from 2 to 7. The group may be straight or branched and, if desired, may be interrupted by an oxygen or sulphur atom or an imino group. Examples of such groups include vinyl and propenyl.

(iii) $R^6$, where $R^6$ is carbocyclic aryl (e.g. $C_{6-12}$ mono- or bicyclic carbocyclic aryl), heterocyclic aryl (e.g. comprising a 5- or 6-membered ring containing at least one of O, N and S), lower cycloalkyl, substituted aryl and substituted cycloalkyl. Examples of this group include phenyl; substituted phenyl e.g. hydroxyphenyl, chlorophenyl, fluorophenyl, tolyl, nitrophenyl, aminophenyl, methoxyphenyl or methylthiophenyl; thien-2- and -3-yl; pyridyl; cyclohexyl; cyclopentyl; cyclopropyl; sydnone; naphthyl; and substituted naphthyl e.g. 2-ethoxynaphthyl.

(iv) $R^6(CH_2)_m$ where $R^6$ has the meaning defined above under (iii) and m is an integer from 1 to 4. Examples of this group include methyl, ethyl or butyl substituted by the various specific $R^6$ groups listed under (iii), e.g. lower cycloalkyl $C_{1-4}$ alkyl and carbocyclic or heterocyclic aryl $C_{1-4}$ alkyl such as benzyl and the appropriate substituted benzyl groups.

3-Position substituents of the above type thus include lower alkanoyloxymethyl groups such as acetoxymethyl and isobutyryloxymethyl, lower alkenoyloxymethyl groups such as crotonyloxymethyl; aroyloxymethyl groups such as benzoyloxymethyl; carbamoyloxymethyl, N-(lower alkyl)carbamoyloxymethyl such as N-methylcarbamoyloxymethyl, and N-(haloalkyl)-carbamoyloxymethyl such as N-(2-1 chloroethyl)carbamoyloxymethyl.

The term "lower" as used in this specification and the accompanying claims to quality aliphatic groups denotes, unless otherwise stated, that the said group may contain up to 6 carbon atoms. "Lower" as used to qualify cycloaliphatic groups indicated that the group may contain 3–7 (e.g. 5–7) carbon atoms.

One class of cephalosporin antibiotics in accordance with the invention comprises compounds of general formula

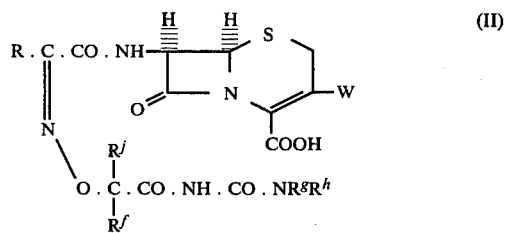

[wherein R is as hereinbefore defined; $R^j$ and $R^f$, which may be the same or different, each represents a hydrogen atom or a methyl group, or $R^j$ and $R^f$ together with the carbon atom to which they are attached form a cyclopentylidene group; $R^g$ and $R^h$, which may be the same or different, each represent a hydrogen atom or a methyl group; and W is selected from:

(i) acetoxymethyl
(ii) carbamoyloxymethyl,
(iii) N-methylcarbamoyloxymethyl, and
(iv) the group —$CH_2SR^w$ wherein $R^w$ is selected from pyridyl, diazolyl, triazolyl, tetrazolyl, thiazolyl, thiadiazolyl, oxadiazolyl, and substituted (e.g. lower alkyl-, carboxymethyl- or phenyl-substituted) versions of these groups such as N-methylpyrid-2-yl, 1-methyltetrazol-5-yl, 1-phenyltetrazol-5-yl; 1-carboxymethyl-tetrazol-5-yl; 5-methyl-1,3,4-thiadiazol-2-yl and 5-phenyl-1,3,4-oxadiazol-2-yl] and non-toxic derivatives thereof.

The compounds according to the invention may be prepared by any convenient method, for example by techniques analogous to those described in British Pat. No. 1,399,086.

Thus according to one embodiment of the invention we provide a process for the preparation of an antibiotic compound of general formula I as hereinbefore defined or a non-toxic derivative thereof which comprises either (A) condensing a compound of the formula

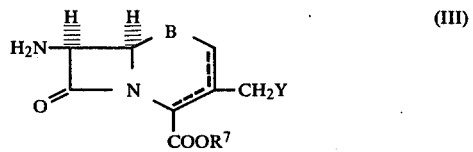

[wherein Y is as defined above; B is $>S$ or $>S \rightarrow >O$ (α- or β-); $R^7$ represents hydrogen or a carboxyl blocking group, e.g. the residue of an ester-forming aliphatic or aralipathic alcohol or an ester-forming phenol, silanol or stannanol (the said alcohol, phenol, silanol or stannanol preferably containing 1–20 carbon atoms) or a symmetrical or mixed anhydride group derived from an appropriate acid; and the dotted line bridging the 2-, 3- and 4-positions indicates that the compound is a ceph-2-em or ceph-3-em compound] or a salt, e.g. an acid addition salt such as a hydrochloride, hydrobromide, sulphate, nitrate, phosphate, methane sulphonate or tosylate, or an N-silylated derivative thereof with an acid of formula

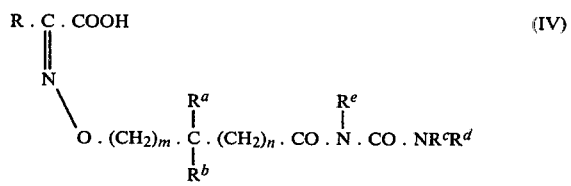

(IV)

wherein R, $R^a$, $R^b$, $R^c$, $R_d$, $R^e$, m and n are as hereinbefore defined) or with an acylating agent corresponding thereto; or (B), reacting a compound of the formula

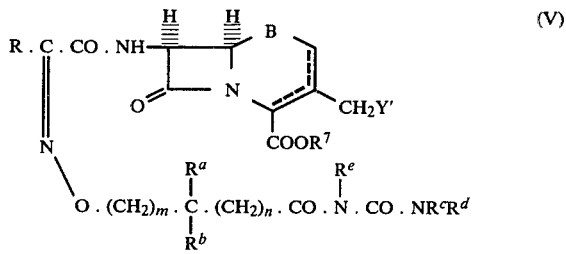

(V)

(wherein B, R, $R^a$, $R^b$, $R^c$, $R^d$, $R^e$, the dotted line, $R^7$, m and n are as hereinbefore defined; and Y' is a replaceable residue of a nucleophile, e.g. an acetoxy, dichloroacetoxy or hydroxy group or a halogen atom such as chlorine, bromine or iodine) with an oxygen or sulphur nucleophile; or (C) reacting a compound of formula

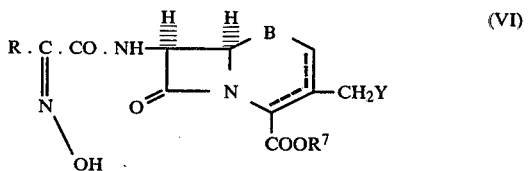

(VI)

(wherein B, R, $R^7$, Y and the dotted line are as defined above) with a compound of formula

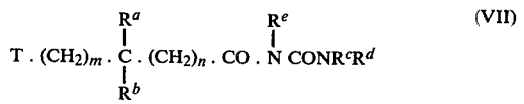

(VII)

(wherein $R^a$, $R^b$, $R^c$, $R^d$, $R^e$, m and n are as hereinbefore defined and T is chloro, bromo or iodo or a sulphonyloxy group, e.g. a mesyloxy or tosyloxy group) preferably in the presence of a base particularly a non-nucleophilic base; whereafter, if necessary and/or desired in each instance, any of the following reaction (D) in any appropriate sequence, are carried out:

(i) conversion of a $\Delta^2$ isomer into the desired $\Delta^3$ isomer,
(ii) reduction of a compound wherein B is >S→O to form a compound wherein B is >S,
(iii) deacylation of a 3-acyloxymethyl compound to form a 3-hydroxymethyl compound,
(iv) acylation of a 3-hydroxymethyl compound to form a 3-acyloxymethyl compound,
(v) carbamoylation of a 3-hydroxymethyl compound to form an unsubstituted or substituted 3-carbamoyloxymethyl compound, and
(vi) removal of carboxyl blocking groups; and finally
(E) recovering the desired compound of formula I or a non-toxic derivative thereof, if necessary after separation of isomers.

Non-toxic derivatives of the compounds of formula I may be formed in any convenient way, for example according to methods well known in the art. Thus, for example, base salts may be formed by reaction of the cephalosporin acid with sodium 2-ethylhexanoate or potassium 2-ethylhexanoate. Biologically acceptable ester derivatives may be formed using conventional esterifying agents. 1-Oxides may be formed by treatment of the corresponding cephalosporin sulphide with an appropriate oxidising agent, for example with a peracid such as metaperiodic acid, peracetic acid, monoperphthalic acid or m-chloroperbenzoic acid, or with t-butyl hypochlorite, this last reagent conveniently being employed in the presence of a weak base such as pyridine.

Acylating agents which may be employed in the preparation of compounds of formula I include acid halides, particularly acid chlorides or bromides. Such acylating agents may be prepared by reacting an acid (IV) or a salt thereof with a halogenating agent e.g. phosphorus pentachloride, thionyl chloride or oxalyl chloride. Treatment of the sodium, potassium or triethylammonium salt of the acid (IV) with oxalyl chloride is advantageous in that under these conditions isomerisation is minimal.

Acylations employing acid halides may be effected in aqueous and non-aqueous reaction media, conveniently at temperatures of from −50° to +50° C., preferably −20° to +30° C., if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula (IV) may themselves be used as acylating agents in the preparation of compounds of formula I. Acylations employing acids (IV) are desirably conducted in the presence of a condensing agent, for example a carbodiimide such as N,N'-dicyclohexylcarbodiimide. Acylation reactions of this type are desirably effected in an anhydrous reaction medium, e.g. methylene chloride, dimethylformamide or acetonitrile.

Acylation may also be effected with other amide-forming derivatives of acids of formula (IV) such as, for example, a symmetrical anhydride or a mixed anhydride (e.g. with pivalic acid or formed with a haloformate such as a lower alkylhaloformate). The mixed or symmetrical anhydride may be generated *in situ*; thus, for example, a mixed anhydride may be generated using N-ethoxycarbonyl-2-ethoxy-1,2-dihydroquinoline.

It will be appreciated that in processes for the preparation of compounds of formula I wherein $R^a$ or $R^b$ represents carboxy it will in many instances be necessary to protect the carboxy group, for example by substitution with a carboxyl blocking group, e.g. a group as hereinbefore defined in connection with $R^7$.

Reaction (C) above is the work of our colleagues WILLIAM KINGSTON WARBURTON and ADRIAN JOHN PIPE.

Reaction (C) above is generally effected under basic conditions serving to effect deprotonation of the hydroxyimino group of the compound of formula (VI), for example in the presence of a base selected from organic bases such as tertiary amines, e.g. triethylamine, 1,5-diazabicyclo-[4,3,0]-non-5-ene and 1,5-diazabicyclo-[5,4,0]-undec-5-ene, and inorganic bases such as metal hydrides, e.g. alkali metal and alkaline earth metal hydrides (for example sodium hydride, lithium hydride and calcium hydride), metal alkyls, e.g. alkali metal lower alkyls (for example butyl lithium) and metal amine salts, e.g. lithium amine salts (for example lithium di-isopropylamide and lithium di-(trimethylsilyl) amide. Alternatively, the base employed in the process according to the invention may comprise a quaternary ammonium salt, for example a bis-tetra-alkyl (e.g. n-butyl)-ammonium salt, of the compound of formula (VI) (when $R^7$ is hydrogen) employed as starting material.

The reaction of the compounds of formulae (VI) and (VII) is conveniently effected in an aprotic solvent selected for example from halogenated hydrocarbons, e.g. dichloromethane, ethers, e.g. tetrahydrofuran, dioxan and diethylene glycol dimethyl ether (diglyme), amides, e.g. dimethylformamide, dimethylacetamide and hexamethyl phosphoramide, sulphoxides, e.g. dimethyl sulphoxide, and sulphones, e.g. sulpholane.

The reaction of the compounds of formulae (VI) and (VII) is preferably effected at a temperature of $-15°$ to $+50°$ C. advantageously $0°$ to $+35°$ C.

According to a particularly preferred embodiment of reaction (C) the compounds of formula (VI) and (VII) are reacted at room temperature in the presence of triethylamine in a dimethylformamide solvent.

Any transformations of substituents at the 3-position which may be necessary in the preparation of particular compounds of formula I may, for example, be effected by methods described in the literature.

Thus, for example compounds of formula I wherein Y represents an ether or thioether group may be prepared as described in British Pat. Nos. 1,241,656; 1,241,657; 1,277,415 and 1,279,402. Compounds wherein Y is the residue of a nucleophile may also be prepared by the reaction of a 3-acetoxymethyl cephalosporin compound with a nucleophile, for example, a sulphur-linking or inorganic nucleophile as described in British Pat. No. 1,012,943; or a sulphur-linking nucleophile as described in British Pat. Nos. 1,059,562; 1,101,423 and 1,206,305. Compounds wherein Y is the residue of a nucleophile may also be prepared by the reaction of a 3-halomethylcephalosporin with any of the nucleophiles disclosed in the above references, such a process being described in British Patent No. 1,241,657, or by the reaction of a 3-halomethylcephalosporin sulphoxide with any of the nucleophiles disclosed in the above references, such a process being described in British Pat. No. 1,326,531. The contents of the above mentioned British Patents are herein incorporated for reference purposes.

Compounds possessing a 3-substituent

—CH$_2$Y wherein Y is a hydroxy group may be prepared by the methods described in British Pat. Nos. 1,121,308, 1,399,086 and 1,474,519.

Carbamoylation of 3-hydroxymethyl compounds may be effected by conventional methods. Thus, for example, a 3-hydroxymethyl cephalosporin may be reacted with an isocyanate of formula $R^k$.NCO (wherein $R^k$ represents a labile substituent group or an alkyl group) to give a compound containing a 3-position substituent having the formula —CH$_2$O.CONHR$^k$ (wherein $R^k$ has the above defined meaning). Where $R^k$ is a labile substituent this substituent may if desired subsequently be cleaved, e.g. by hydrolysis, to form a 3-carbamoyloxymethyl group. Labile groups $R^k$ which are readily cleavable upon subsequent treatment include chlorosulphonyl and bromosulphonyl; halogenated lower alkanoyl groups such as dichloroacetyl and trichloroacetyl; and halogenated lower alkoxycarbonyl groups such as 2,2,2-trichloroethoxycarbonyl. These labile $R^k$ groups may generally be cleaved by acid or base catalysed hydrolysis (e.g. by base catalysed hydrolysis using sodium bicarbonate).

A ceph-2-em reaction product may also be oxidised to yield the corresponding ceph-3-em 1-oxide, for example by reaction with a peracid as mentioned previously; the resulting sulphoxide may, if desired, subsequently be reduced as described hereinafter to yield the corresponding ceph-3-em sulphide.

Where a compound is obtained in which B is $>S{\to}O$ this may be converted to the corresponding sulphide by, for example, reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of $-20°$ to $+50°$ C.

Where a compound of formula I is obtained as a mixture of isomers, the syn isomer may be obtained by, for example, conventional methods such as crystallisation or chromatography.

Acids of formula IV and acid halides and anhydrides corresponding thereto are novel.

For use as starting materials for the preparation of compounds of general formula I according to the invention, compounds of general formula IV and acid halides and anhydrides corresponding thereto in their syn isomeric form or in the form of mixtures of the syn isomers and the corresponding anti isomers containing at least 90% of the syn isomer are preferably used.

Acids IV may be prepared by etherification of an acid of formula

(where R has the above-defined meaning) by reaction with a compound of general formula

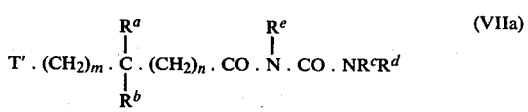

(wherein $R^a$, $R^b$, $R^c$, $R^d$, $R^e$, m and n are as hereinbefore defined and T' is halogen such as chloro, bromo, or iodo; or sulphonate such as tosylate. Separation of isomers may be effected either before or after such etherification. The etherification reaction is desirably carried out in the presence of a base, e.g. potassium t-butoxide or sodium hydride, and is preferably conducted in an organic solvent, for example dimethylsulphoxide, a cyclic ether such as tetrahydrofuran or dioxan, or an N,N-disubstituted amide such as dimethylformamide. Under these conditions the configuration of the oximino group is substantially unchanged by the etherification reaction. This process is particularly useful in the preparation of acids (IV) in which both $R^a$ and $R^b$ are hydrogen. Separation of isomers may be effected at any appropriate stage in the reaction sequence.

A further method of preparing acids of general formula (IV) is by reaction of a glyoxylic acid of formula

  (IX)

(wherein R is as defined above) with a compound of formula

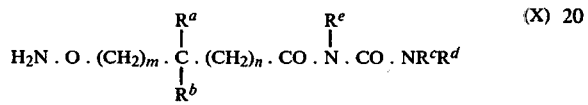  (X)

(wherein $R^a$, $R^b$, $R^c$, $R^d$, $R^e$ m and n are as defined above). Reaction of (IX) with (X) may be followed where necessary by the separation of syn and anti isomers.

The acids of formula (IV) may be converted to the corresponding acid halides and anhydrides by conventional methods.

Carboxyl blocking groups $R^7$ used in the preparation of compounds of formula I or in the preparation of necessary starting materials are desirably groups which may readily be split off at a suitable stage in the reaction sequence, conveniently as the last stage. It may, however, be convenient in some instances to employ biologically acceptable, metabolically labile carboxyl blocking groups such as acyloxymethyl groups (e.g. acetoxymethyl, acetoxyethyl and pivaloyloxymethyl) and retain these in the final product to give a biologically acceptable ester derivative of a compound of formula I.

Suitable carboxyl blocking groups are well known in the art, a list of representative blocked carboxyl groups being included in British Pat. No. 1,399,086. Preferred blocked carboxyl groups include aryl lower alkoxycarbonyl groups such as p-methoxybenzyloxylcarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature. For example, acid-, base- or enzymically- catalysed hydrolysis and reductive methods are applicable in many cases.

The antibiotic compounds of the invention, e.g. compounds of formula I and non-toxic derivatives thereof, may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients The antibiotic compounds according to the invention may be formulated for injection and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The antibiotic compounds may also be presented in a form suitable for absorption by the gastro-intestinal tract, e.g. as tablets or capsules. The antibiotic compounds may also be formulated as suppositories, e.g. containing conventional suppository bases such as cocoa butter or other glyceride.

Compositions for veterinary medicine may, for example, be formulated as intramammary preparations in either long acting or quick-release bases.

The compositions may contain from 0.1% upwards, e.g. 0.1-99%, preferably from 10-60% of the active material, depending on the method of administration. When the compositions comprise dosage units, each unit will preferably contain 50-1500 mg of the active ingredient. The dosage as employed for adult human treatment will preferably range from 500 to 5000 mg per day, depending on the route and frequency of administration, although in treating some infections higher daily doses may be required.

The antibiotic compounds according to the invention may be administered in combination with other therapeutic agents such as antibiotics, for example penicillins or other cephalosporins.

The following examples illustrate the invention. All temperatures are in °C. The structures of the products were verified by p.m.r. and i.r. spectroscopy.

PREPARATION 1

1-Bromocyclopentanecarbonyl Chloride

1-Bromocyclopentanecarboxylic acid (6.4 g) was refluxed with thionyl chloride (6 ml) for 40 min. Removal of the thionyl chloride and distillation gave the acid chloride 5.6 g, b.p. 85°-87°/17 mm $\nu_{max}^{CS_2}$ 1780 cm$^{-1}$ (COCl), $\tau$ (CDCl$_3$) ca 7.2-8.4 (cyclopentyl).

PREPARATION 2

1-Bromo-1-ureidocarbonylcyclopentane

1-Bromocyclopentanecarbonyl chloride (5.5 g) was stirred with urea (3.15 g) at 80° for 30 min. The mixture was cooled and water (30 ml) was added, then the pH was brought to 7. The solid was filtered off and recrystallised twice from ethanol, giving the acylurea, 0.75 g, m.p. 189°-191°, $\nu_{max}$ (Nujol) 3420, 3300, 3220 (NH,NH$_2$), 1702, 1690 and 1585 cm$^{-1}$ (CONH, CONH$_2$), $\tau$ (DMSO d$_6$) - ca 0.2 (NH), - ca 2.4 and - ca 2.6 (NH$_2$), ca 7.3-8.5 (cyclopentyl).

PREPARATION 3 syn-Triethylammonium triphenylmethoxyiminofur-2-ylacetate

Triethylamine (5.05 g; 6.9 ml) was added to a stirred suspension of syn-hydroxyiminofur-2-ylacetic acid (3.10 g) in dry dichloromethane (30 ml). The solid dissolved rapidly and then the triethylamine salt partially separated. A solution of chlorotriphenylmethane (6.15 g) in dry dichloromethane (30 ml) was added to the slurry and the mixture stirred for 1 hr before being evaporated to dryness under reduced pressure. The residual solid was stirred for 1 hr with water (100 ml), filtered off, dried and then stirred with ether (50 ml). The title salt was filtered off and dried (8.95 g). τ (DMSO d₆; 60 MHz) 2.34 and 3.48 (syn-2-furyl protons) 2.63 (m, Ph protons), 6.95 (q, J 7 Hz; N—CH₂—CH₃) and 8.80 (t, J 7 Hz; N—CH₂CH₃).

PREPARATION 4 syn(6R,7R)-3-Carbamoyloxymethyl-7-(hydroxyiminofur-2-ylacetamido)ceph-3-em-4-carboxylic acid, sodium salt A solution of syn-triethylammonium triphenylmethoxyiminofur-2-ylacetate (5.0 g) in dry dichloromethane (30 ml) containing dimethylformamide (one drop) was cooled to −5° to −10° and treated with oxalyl chloride (0.86 ml). The mixture was stirred for 0.75 hr as the temperature was allowed to rise to 0°. The mixture was evaporated under reduced pressure finally under high vacuum at below 0°. The residual solid was triturated with dry ether (ca 80 ml), filtered as rapidly as possible, and the filtrate evaporated to dryness under reduced pressure. The residual foam was triturated with dry petroleum (b.p. 40°-60°) and then evaporated to dryness finally under high vacuum to give a crystalline mass of the acid chloride (4.8 g).

The acid chloride (4.8 g) was dissolved in dry dichloromethane (40 ml) and added dropwise with stirring during 20 min to a solution, at −5°, of diphenylmethyl (6R,7R)-7-amino-3-carbamoyloxymethylceph-3-em-4-carboxylate (5.15 g) in a mixture of dry dichloromethane (60 ml) and 1,2-epoxypropane (5 ml). The mixture was allowed to warm to 0° during 20 min and to room temperature during a further 30 min. The mixture was shaken with dilute sodium bicarbonate solution and the organic phase separated and filtered from a small amount of amorphous material. The dichloromethane solution was washed sequentially with dilute hydrochloric acid, water, dilute sodium bicarbonate solution and water. The solution was dried and evaporated to dryness under reduced pressure. The residue was triturated with dry ether (ca 30 ml) and the crystalline ester collected (6.29 g). A sample recrystallised from benzene gave syn-diphenylmethyl (6R,7R)-3-carbamoyloxymethyl-7-(triphenylmethoxyiminofur-2-yl-acetamido)-ceph-3-em-4-carboxylate. m.p. 178° (dec) τ (DMSO d₆; 100 MHz) values include -0.05 (d J 8 Hz; —CONH), 3.97 (d, d J 4 and 8 Hz; C-7 H) 2.27 and 3.40 (syn 2-furyl and NH₂), 3.06 (s, —CHPh₂), 2.69 (phenyl protons), 4.67 (d, J 4 Hz; C-6 H), 5.15 and 5.38 (AB quartet; J 13 Hz; —CH₂O) and 6.39 (broad s, C-2 H₂).

The above ester (4.0 g) was stirred in an ice-bath with anisole (8 ml) and trifluoroacetic acid (25 ml) was added. The dark brown solution was stirred at ice-bath temperature for ½ hr and then diluted with iced water (ca 50 ml). The mixture was evaporated to small bulk under high vacuum and the residue dissolved in ethyl acetate and shaken with an excess of sodium bicarbonate solution. The alkaline extract was washed twice more with ethyl acetate and then acidified to pH 2 with hydrochloric acid under a layer of ethyl acetate. The organic layer was separated, combined with two more extracts, dried and evaporated to dryness under reduced pressure. The residual foam was triturated with ether and then filtered off and washed with ether to give the title acid (1.817 g).

The acid (0.50 g) was stirred with acetone (10 ml) and water (0.15 ml) added to give a clear solution. A solution of sodium 2-ethylhexanoate (0.215 g) in acetone (6 ml) was added and the flocculent precipitate stirred for ½ hr. The solid was filtered and washed with acetone to give the title salt (0.343 g). τ (D₂O; 100 MHz) values include 2.32, 3.13 and 3.35 (syn-2-furyl protons), 4.14 (d, J 4 Hz; C-7 H), 4.76 (d, J 4 Hz; C-6-H) and 6.29 and 6.61 (AB quartet J 17 Hz; C-2-H₂).

EXAMPLE 1

(6R,7R)-3-Acetoxymethyl-7-[Z-2-(fur-2-yl)-2-(2-ureidocarbonylprop-2-yloxyimino)acetamido]-ceph-3-em-4-carboxylic acid 2-Bromo-2-methylpropionylurea (1.65 g) was added to a stirred solution of (6R,7R)-3-acetoxymethyl-7-[Z-2-(fur-2-yl)-2-hydroxyiminoacetamido]-ceph-3-em-4-carboxylic acid sodium salt (1.13 g) and triethylamine (0.73 ml) in dimethylformamide (30 ml). The mixture was stirred for 48 hr, then ethyl acetate (100 ml) was added and the solution was washed with 2N-hydrochloric acid (3×30 ml) and extracted with sodium hydrogen carbonate solution (3×30 ml). The aqueous extract was acidified with 2N-hydrochloric acid and extracted with ethyl acetate (3×30 ml). The extract was dried (Na₂SO₄) and evaporated. The residue was dissolved in a little acetone and added dropwise to stirred light petroleum (b.p. 40°-60°; 150 ml), giving the title-compound, 0.87 g, [α]_D^25 +84° (c 1, DMSO), λ_max (EtOH) 275 nm (ε 15,700), ν_max (Nujol) 3700-2100 (bonded OH), 3420, 3300, 3280 (NH, NH₂), 1784 (β-lactam), 1735 (acetate), 1710 (CO₂H), 1565 cm⁻¹ (CONH, CONHCONH₂), τ (DMSO d₆) included 0.1 (CONH), 0.68, 2.25 and 2.7 (CONHCONH₂), 2.18, 3.21, 3.38 (α-furyl), 4.78 (6 H), 4.09 (7 H), 4.98, 5.3 (3 —CH₂), 6.28, 6.5 (2 —CH₂), 7.92 (OCOCH₃), 8.55 (CMe₂).

EXAMPLE 2

(6R,7R)-3-Carbamoyloxymethyl-7-[Z-2-(fur-2yl)-2-ureidocarbonylprop-2-yloxyimino)acetamido]-ceph-3-em-4-carboxylic acid This was prepared from 2-bromo-2-methylpropionylurea and (6R,7R)-3-carbamoyloxymethyl-7-[Z-2-(fur-2-yl)-2-hydroxyiminoacetamido]-ceph-3-em-4-carboxylic acid sodium salt by the method described in Example 1. Yield 52%; λ_max (EtOH) 274 nm (ε 15,300), ν_max (Nujol) 3420, 3300, 3100 (—NH—, NH₂), 3700-2100 (bonded OH), 1782 (β-lactam), 1680, 1565, 1545 (—CONH, CONHCONH₂) 1705 cm⁻¹ (CO₂H,—OCONH₂), τ (DMSO d₆) 2.2, 2.62 (NHCONH₂), 1.62 (CONHCO), 8.5 (C(Me)₂), 3.19, 3.3, 2.1 (fur-2-yl), 4.1 (7 H), 4.72 (6 H), 6.29, 6.49 (2 CH₂), 5.02, 5.32 (3 CH₂), 3.4 (OCONH₂).

EXAMPLE 3

(6R,7R)-3-Acetoxymethyl-7-[Z-2-(fur-2-yl)-2-(1-ureidocarbonylcyclopent-1-yloximino)acetamido]-ceph-3-em-4-carboxylic acid This was prepared from 1-bromo-1-ureidocarbonylcyclopentane and (6R,7R)-3-acetoxymethyl-7-[Z-2-(fur-2-yl)-2-hydroxyiminoacetamido]-ceph-3-em-4-carboxylic acid sodium salt, in a similar manner to Example 2. [α]_D^22 +95° (c 0.55, DMSO), λ_max(EtOH) 275 nm (ε16,500), ν_max (Nujol) 3420, 3300 (NH, NH₂), 3700-2100 (bonded OH), 1788 (β-lactam), 1735 (acetate), 1710, 1690, 1565, 1550 cm⁻¹ (CONH, CONHCONH₂), τ (DMSO d₆) 7.92 (OAc), 4.95, 5.28 (dd J 13) (3 —CH₂), 6.23, 6.49 (dd, J 18) (2 —CH₂), 4.71 (d, J=5) (6 H), 4.09 (dd J=5, 8) (7 H), 0.02 (d, J=8) (CONH), 2.11, 3.19, 3.32 (furyl), 7.9–8.3 (cyclopentyl), 0.65 (CONHCO), 2.17, 2.64 (CONH$_2$). Yield: 85%.

EXAMPLE 4

(6R,7R)-3-Acetoxymethyl-7-{Z-2-(fur-2-yl)-2-[2-(3-methylureidocarbonyl)prop-2-yloxyimino]acetamido}-ceph-3-em-4-carboxylic acid This compound was prepared from 1-(2-bromo-2-methylpropionyl)-3-methylurea and (6R,7R)-3-acetoxymethyl-7-[Z-2-(fur-2-yl)-2-hydroxyiminoacetamido]-ceph-3-em-4-carboxylic acid sodium salt by the method described in Example 1. $[\alpha]_D^{22}+84.6°$ (c 0.65, DMSO), $\lambda_{max}$(EtOH) 274 nm ($\epsilon$ 16,900), $\nu_{max}$(Nujol) 3340 (NH), 3700–2100 (bonded OH), 1790 ($\beta$-lactam), 1740 (OCOCH$_3$), 1700 (CO$_2$H), 1690, 1540 cm$^{-1}$ (—CONH—, —CONHCONH—), $\tau$ (DMSO d$_6$) 2.25, 3.2, 3.35 (fur-2-yl), 8.51, 8.52 (C(Me)$_2$), 0.5 (—CO<u>N</u>HCO), 1.75 (CO<u>N</u>HMe), 7.28 (CON<u>HM</u>e), 4.1 (7 H), 4.75 (6 H), 6.28, 6.50 (2 CH$_2$), 4.97, 5.29 (3 CH$_2$), 7.9 (OCOCH$_3$). Yield: 76%.

EXAMPLE 5

(6R,7R)-3-Acetoxymethyl-7-[E-2-(thien-2-yl)-2-(2-ureidocarbonylprop-2-yloxyimino)acetamido]-ceph-3-em-4-carboxylic acid This compound was prepared from 2-bromo-2-methylpropionylurea and (6R,7R)-3-acetoxymethyl-7-[E-2-hydroxyimino-2-(thien-2-yl)acetamido]-ceph-3-em-4-carboxylic acid sodium salt dihydrate by the method described in Example 1. $[\alpha]_D^{23}+100°$ (c 0.75, DMSO), $\lambda_{max}$(EtOH) 263.5 nm ($\epsilon$ 13,800), $\nu_{max}$(Nujol) 3420, 3280 (NH, NH$_2$), 3700–2000 (bonded OH), 1782 ($\beta$-lactam), 1700 (—CO$_2$H), 1560 (—CONH, CONHCONH$_2$), 1735 cm$^{-1}$ (OCOCH$_3$), $\tau$ (DMSO d$_6$) -0.01 (CONH), 4.0 (7 H), 4.7 (6 H), 6.22, 6.43 (2 —CH$_2$), 0.55 (—CO<u>N</u>HCO—), 4.91, 5.22 (3 CH$_2$), 7.95 (OCOCH$_3$), 2.22, 2.68, 2.8 (thien-2-yl), 8.45 (C(Me)$_2$), 2.2, 2.6 (—CONH$_2$). Yield: 83%.

EXAMPLE 6

(6R,7R)-3-Acetoxymethyl-7-[Z-2-(fur-2-yl)-2-ureidocarbonylmethoxyiminoacetamido]-ceph-3-em-4-carboxylic acid This compound was prepared from iodoacetylurea and (6R,7R)-3-acetoxymethyl-7-[Z-2-(fur-2-yl)-2-hydroxyiminoacetamido]-ceph-3-em-4-carboxylic acid sodium salt by the method described in Example 1. $\lambda_{max}$(EtOH) 274 nm ($\epsilon$ 17,300), $\nu_{max}$(Nujol) 3420, 3260 (—NH—, —NH$_2$), 3700–2100 (bonded OH), 1780 ($\beta$-lactam), 1720(—CO$_2$H, acetate), 1700, 1570, 1545 cm$^{-1}$ (CONH, CONH$_2$), $\tau$ (DMSO d$_6$) 2.11, 3.3, 3.18 (furyl), 5.28 (—O—C<u>H</u>$_2$—), 0.09 (—CO<u>N</u>HCO—), 2.5 (CON<u>H</u>$_2$), 0.11 (CO<u>N</u>H), 4.1 (7 H), 4.78 (6 H), 6.29, 6.51 (2 —CH$_2$), 4.95, 5.28 (3 —CH$_2$), 7.93 (C<u>H</u>$_3$CO—). Yield: 34%.

EXAMPLE 7

(a) 1-(2-Bromo-2-methylpropionyl)-3,3-dimethylurea

2-Bromo-2-methylpropionyl bromide (8.9 g) in dichloromethane (20 ml) was added dropwise at 0° to a stirred suspension of 1,1-dimethylurea (3.4 g) in dichloromethane (25 ml) and triethylamine (16 ml). The mixture was stirred for 4 hr. at 22° and the solvent was evaporated. The residue was stirred with saturated sodium hydrogen carbonate solution (40 ml) and extracted with ethyl acetate (3×20 ml). The ethyl acetate solution was dried and evaporated. The residue was stirred with light petroleum (b.p. 40°–60°, 50 ml) and the remaining solid was filtered off and suspended in sodium hydrogen carbonate solution and extracted into ethyl acetate (2×20 ml). The ethyl acetate solution was dried and evaporated, leaving the urea as a pale brown solid, 1.4 g, m.p. 98°–100°, $\nu_{max}$(Nujol) 3400, 3370 (NH), 1742, 1685 cm$^{-1}$ (—CONH.CON—), $\tau$ (DMSO d$_6$) 8.06 (—C(Me)$_2$), 7.01 (-N(Me)$_2$), 1.6 (—CON<u>H</u>CO—).

(b)
(6R,7R)-3-Acetoxymethyl-7-[Z-2-{2-(3,3-dimethylureidocarbonyl)prop-2-yloxyimino}-2-(fur-2-yl)acetamido]-ceph-3-em-4-carboxylic acid This compound was prepared from 1-(2-bromo-2-methylpropionyl)-3,3-dimethylurea and (6R,7R)-3-acetoxymethyl-7-[Z-2-(fur-2-yl)-2-hydroxyiminoacetamido]-ceph-3-em-4-carboxylic acid sodium salt by the method described in Example 1. $\lambda_{max}$ (EtOH) 275 nm ($\epsilon$ 16,500), $\nu_{max}$ (Nujol) 3260 (NH), 3700–2100 (bonded OH), 1788 ($\beta$-lactam), 1735 (acetate), 1720 (—CO$_2$H), 1670, 1540 cm$^{-1}$ (—CONH), $\tau$ (DMSO d$_6$) 7.09 (N(Me)$_2$), 0.97 (—CO<u>N</u>HCO—), 8.5 (C(Me)$_2$), 2.06, 3.28, 3.16 (furyl), 0.18 (CONH), 4.01 (7 H), 4.71 (6 H), 6.25, 6.46 (2—CH$_2$—), 4.97, 5.29 (3—CH$_2$—), 7.98 (CH$_3$CO). Yield: 59%.

EXAMPLE 8

(a) Methyl Z-2-Hydroxyimino-2-phenylacetate

Z-2-(Hydroxyimino)-2-phenylacetic acid (4.0 g) in ether (50 ml) was methylated by the addition of a slight excess of diazomethane in ether. The excess of diazomethane was destroyed by acetic acid, and the solution was washed with saturated sodium hydrogen carbonate solution, dried (Na$_2$SO$_4$) and evaporated, leaving the ester, 4.16 g, $\nu_{max}$ (CHBr$_3$) 3600 (OH), 3300 (bonded OH), 1722 cm$^{-1}$ (—CO$_2$R), $\tau$ (DMSO d$_6$) —2.0 (—OH), 6.08 (—CH$_3$), 2.47 (Phenyl).

(b) Methyl Z-2-Phenyl-2-(2-ureidocarbonylprop-2-yloxyimino)acetate

Sodium hydride (80% dispersion in oil, 0.44 g) was added to a solution of methyl Z-2-hydroxyimino-2-phenylacetate (2.6 g) in benzene (10 ml) and dimethylformamide (8 ml) and the mixture was stirred for 30 min. 2-Bromo-2-methylpropionylurea (3.0 g) was added and the mixture was stirred for 20 hr. Water (50 ml) was added and the solution was extracted with ethyl acetate (4×25 ml). The extracts were washed with water, dried (Na$_2$SO$_4$) and evaporated. The residue was purified by chromatography on silica gel in light petroleum (b.p. 40°–60° ) and ethyl acetate (1:1 v/v), giving the ester as a white solid, 3.3 g $\nu_{max}$ (Nujol) 3400, 3270, 3240, 3140 (—NH; —NH$_2$), 1748, 1728, 1703 cm$^{-1}$ (—CO$_2$R, —CONHCONH$_2$), $\tau$(DMSO d$_6$) 2.3–2.5 (Phenyl), 6.0 (Methyl), 8.42 (C(Me)$_2$), 0.9 (CON<u>H</u>CO), 2.0–2.8 (CONH$_2$).

(c) Z-2-Phenyl-2-(2-ureidocarbonylprop-2-yloxyiminoacetic acid

Aqueous sodium hydroxide solution (N, 6.6 ml) was added dropwise to a stirred suspension of methyl Z-2-phenyl-2-(2-ureidocarbonylprop-2-yloxyimino)acetate (1.0 g) in methanol (25 ml) at 0°. The mixture was stirred for 18 hr at 25°, the pH adjusted to 7 and the methanol evaporated. The residue was dissolved in sodium hydrogen carbonate solution and the solution was washed with ethyl acetate, acidified (2N- hydrochloric acid) and extracted into ethyl acetate (3×15 ml). The extracts were dried (Na$_2$SO$_4$) and evaporated and the residue was washed with carbon tetrachloride (10 ml), leaving the acid, 170 mg, $\lambda_{max}$ (EtOH) 252 nm ($\epsilon$11,800), $\nu_{max}$ (Nujol) 3600–2100 (bonded OH), 3430, 3280 (NH, NH$_2$), 1720 (—CO$_2$H), 1652, 1613, 1580 cm$^{-1}$ (—CONHCONH$_2$). $\tau$(DMSO d6) 2.47 (Phenyl), 8.47 (C(Me)$_2$), 2.0 (CO<u>N</u>HCO), 2.2–2.8 (—CONH$_2$).

(d) Diphenylmethyl (6R,7R)-3-(1-Methyltetrazol-5-yl-thiomethyl)-7-[Z-2-phenyl-2-(2-ureidocarbonylprop-2-yloxyimino)acetamido]-ceph-3-em-4-carboxylate A solution of Z-2-phenyl-2-(2-ureidocarbonylprop-2-yloxyimino)acetic acid (460 mg) in dichloromethane (6 ml) and dimethylformamide (2 ml) was added slowly to a stirred solution of dicyclohexylcarbodiimide (370 mg) and diphenylmethyl (6R,7R)-3-(1-methyltetrazol-5-ylthiomethyl)-7-aminoceph-3-em-4-carboxylate (790 mg) in dichloromethane (10 ml) and dimethylformamide (3 ml) and the mixture was stirred for 20 hr. The solution was filtered, the filtrate was evaporated, and the residue was dissolved in ethyl acetate (50 ml). The filtered solution was washed with 2N- hydrochloric acid (2×15 ml) and saturated sodium hydrogen carbonate solution (2×15 ml), dried (Na$_2$SO$_4$) and evaporated. The residue was purified on silica gel plates in light petroleum-ethyl acetate (1:1 v/v) to give the ester, 580 mg, $\lambda_{max}$ (Nujol) 3400, 3280 (NH, NH$_2$), 1788 ($\beta$-lactam), 1720, 1710 (—CO$_2$R), 1685, 1670 cm$^{-1}$ (—CONHCONH$_2$, —CONH—), $\tau$(DMSO d6) 0.60 (—CO<u>N</u>HCO—), 8.59 (—C(Me)$_2$—), 2.0–2.9 (Phenyls), —0.06 (—CONH—), 3.87 (7 H), 4.62 (6H), 5.9, 6.5 (2—CH$_2$—), 5.59, 5.79 (3—CH$_2$—), 6.09 (—N—<u>Me</u>), 3.0 (—<u>CH</u> Ph$_2$).

(e) (6R,7R)-3-(1-Methyltetrazol-5-ylthiomethyl)-7-[Z-2-phenyl-2-(2-ureidocarbonylprop-2-yloxyimino)acetamido]-ceph-3-em-4-carboxylic Acid Diphenylmethyl (6R,7R)-3-(1-methyltetrazol-5-ylthiomethyl)-7-[Z-2-phenyl-2-(2-ureidocarbonylprop-2-yloxyimino)acetamido]-ceph-3-em-4-carboxylate (580 mg) was stirred for 10 min with trifluoroacetic acid (6 ml) and anisole (4 ml). The solution was poured into saturated sodium hydrogen carbonate solution (60 ml) and washed with ethyl acetate (3×15 ml). The aqueous layer was acidified and extracted with ethyl acetate (3×15 ml), and the extracts were dried and evaporated. The residual gum was dissolved in a little acetone and the solution was slowly added to vigorously stirred light petroleum (b.p. 40°–60°, 100 ml), giving the acid as a yellow powder, 180 mg, $\lambda_{max}$ (Etoh) 257.5 nm ($\epsilon$15,100), $\nu_{max}$ (Nujol) 3400, 3280 (NH, NH$_2$), 3700–2100 (bonded OH), 1782 ($\beta$-lactam), 1700 (—CO$_2$H), 1685, 1675, 1560 cm$^{-1}$ (—CONH—, —CONH$_2$), $\tau$(DMSO d6) 2.42 (Phenyl), 8.5 (—C(-Me)$_2$—), 0.6 (—CO<u>N</u>HCO—), 2.0–2.8 (—CON<u>H</u>$_2$), 0.0 (—CO<u>N</u>H—), 4.01 (7 H), 4.75 (6 H), 6.21 (2—CH$_2$—), 5.62 (3—CH$_2$—), 6.0 (N—C<u>H</u>$_3$).

EXAMPLE 9

(a) 1-(2-Bromo-2-methylpropionyl)-1,3-dimethylurea

This compound was prepared similarly to 1-(2-bromo-2-methylpropionyl)-3,3-dimethylurea in Example 7a from 2-bromo-2-methylpropionyl bromide and 1,3-dimethylurea. It was obtained in 38% yield as a yellow oil, $\nu_{max}$ (Nujol) 3330 (NH), 1730, 1700 cm$^{-1}$ (CON. CON). $\tau$(DMSO d6) 6.44 (NMe) 7.13 (d,J 5; NHMe), 7.95 (CMe$_2$).

(b) (6R,7R)-3-Acetoxymethyl-7-[Z-2-{1,3-dimethylureidocarbonylprop-2-yloxyimino}-2-(fur-2-yl)acetamido]-ceph-3-em-4-carboxylic acid This compound was prepared from 1-(2-bromo-2-methylpropionyl)-1,3-dimethylurea and (6R,7R)-3-acetoxymethyl-7-[Z-2-(fur-2-yl)-2-hydroxyiminoacetamido]-ceph-3-em-4-carboxylic acid sodium salt by the method described in Example 1. Yield 73%, $\lambda_{max}$ (EtOH) 274 nm ($\epsilon$12,500), $\nu_{max}$ (Nujol) 3300 (NH), 3700–2100 (bonded OH), 1789 ($\beta$-lactam), 1730 (CO$_2$H), 1685, 1535 (CONH), $\tau$(DMSO d6) 0.18 (CONH), 2.11, 3.28, 3.31 (furyl), 4.11, (7H), 4.77 (6H), 4.97, 6.29 (3—CH$_2$), 6.29, 6.49 (2—CH$_2$), 6.75 (NMe), 7.28 (NHMe), 7.93 (OAc), 8.41 (CMe$_2$).

Pharmaceutical compositions according to the invention may be formulated according to the following Examples.

EXAMPLE A (a) Dry Powder for Injection

The sterile sodium salt of (6R,7R)-3-acetoxy-methyl-7-[Z-2-(fur-2-yl)-2-(1-ureidocarbonylcyclopent-1-yloximino)acetamido]ceph-3-em-4-carboxylic acid is filled into glass vials, the claimed contents of each container being 500 mg and 1.0 g of the cephalosporin. Filling is carried out aseptically under a blanket of nitrogen. The vials are closed using rubber discs or plugs held in position by aluminum sealing rings, thereby preventing gaseous exchange or ingress of microorganisms. It would be possible to reconstitute the product by dissolving in water for injections or other suitable sterile vehicle shortly before administration.

(b) Intramammary Injection (for a lactating cow)

Percentage Composition (w/w)

| | |
|---|---|
| Sodium salt of the cephalosporin used in (a): | 8.33 |
| Vehicle to: | 100.00 |
| Vehicle: Tween 60 | 3.00 |
| White Beeswax | 6.00 |
| Arachis Oil | 91.00 |

The three ingredients of the vehicle are heated together at 150° C. for one hour and then cooled to room temperature with stirring. The sterile antibiotic, finely powdered, is added aseptically to this vehicle and the product refined with a high speed mixer. The preparation is filled aseptically into sterile containers such as collapsible aluminium tubes or plastic syringes. The fill weight is 3.0 g, each container holding 250 mg of the cephalosporin acid as sodium salt. The product would be intended for administration into the mammary gland through the teat canal.

We claim:

1. An antibiotic compound of the formula

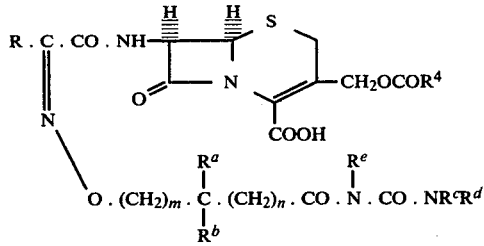

wherein R is a phenyl, thienyl or furyl group; $R^a$ and $R^b$, which may be the same or different, are each hydrogen, $C_{1-4}$ alkyl, $C_{2-4}$ alkenyl, $C_{3-7}$ cycloalkyl, phenyl, naphthyl, thienyl or furyl or $R^a$ and $R^b$ together with the carbon atom to which they are attached form a $C_{3-7}$ cycloalkylidene or cycloalkenylidene group; $R^c$ and $R^d$, which may be the same or different, each represents a hydrogen atom or a $C_{1-4}$ alkyl group; or $R^c$ and $R^d$ together with the nitrogen atom to which they are attached form an unsubstituted saturated or unsaturated heterocyclic ring of 5–7 ring members or such a ring monosubstituted by lower alkyl; $R^e$ represents hydrogen or $C_{1-4}$ alkyl; $R^4$ represents $C_{1-7}$ alkyl; $C_{1-7}$ alkyl interrupted by an oxygen or sulphur atom or an imino group; $C_{1-7}$ alkyl monosubstituted by cyano, carboxy, lower alkoxycarbonyl, hydroxy, carboxycarbonyl, halo or amino; $C_{2-7}$ alkenyl, $C_{2-7}$ alkenyl interrupted by an oxygen or sulphur atom or an imino group; lower cycloalkyl; phenyl; hydroxyphenyl; chlorophenyl; fluorophenyl; tolyl; nitrophenyl; aminophenyl methoxyphenyl; methylthiophenyl; lower cycloalkyl $C_{1-4}$ alkyl or phenyl $C_{1-4}$ alkyl; and m and n are each 0 to 1 such that the sum of m and n is 0 or 1 or a physiologically acceptable salt, ester, 1-oxide or solvate thereof.

2. A compound as claimed in claim 1 having the formula

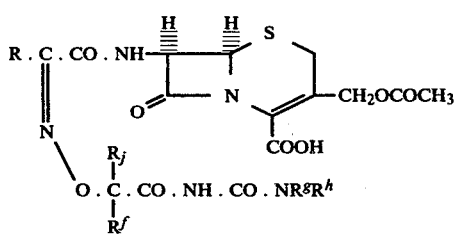

wherein R is as defined in claim 16; $R^j$ and $R^f$, which may be the same or different, each represents a hydrogen atom or a methyl group, or $R^j$ and $R^f$ together with the carbon atom to which they are attached form a cyclopentylidene group; and $R^g$ and $R^h$ which may be the same or different, each represent a hydrogen atom or a methyl group; or a physiologically acceptable salt, ester, 1-oxide or solvate thereof.

3. A compound is claimed in claim 1 which is a syn isomer essentially free from the anti isomer.

4. A compound as claimed in claim 1 wherein $R^4$ is methyl.

5. A compound as claimed in claim 1, said compound being (6R,7R)-3-acetoxymethyl-7-[2-(fur-2-yl)-2-(2-ureidocarbonylprop-2-yloxyimino)acetamido]ceph-3-em-4-carboxylic acid (syn isomer).

6. A compound as claimed in claim 1, said compound being
(6R,7R)-3-acetoxymethyl-7-[2-(fur-2-yl)-2-(1-ureidocarbonylcyclopent-1-yloximino)acetamido]-ceph-3-em-4-carboxylic acid (syn isomer).

7. A compound as claimed in claim 1, said compound being
(6R,7R)-3-acetoxymethyl-7-{2-(fur-2-yl)-2-[2-(3-methylureidocarbonyl)prop-2-yloxyimino]acetamido}ceph-3-em-4-carboxylic acid (syn isomer).

8. A compound as claimed in claim 1, said compound being
(6R,7R)-3-acetoxymethyl-7-[2-(thien-2-yl)-2-(2-ureidocarbonylprop-2-yloxyimino)acetamido]-ceph-3-em-4-carboxylic acid (syn isomer).

9. A compound as claimed in claim 1, said compound being
(6R,7R)-3-acetoxymethyl-7-[2-(fur-2-yl)-2-ureidocarbonylmethoxyiminoacetamido]ceph-3-em-4-carboxylic acid (syn isomer).

10. A compound as claimed in claim 1, said compound being
(6R,7R)-3-acetoxymethyl-7-[2-{2-(3,3-dimethylureidocarbonyl)prop-2-yloxyimino}-2-(fur-2-yl)acetamido]ceph-3-em-4-carboxylic acid (syn isomer).

11. A compound as claimed in claim 1, said compound being
(6R,7R)-3-acetoxymethyl-7-[2-{1,3-dimethylureidocarbonyl-prop-2-yloxyimino}-2-(fur-2-yl)acetamido]ceph-3-em-4-carboxylic acid (syn isomer).

* * * * *